United States Patent
Ergler et al.

(10) Patent No.: US 10,684,379 B2
(45) Date of Patent: Jun. 16, 2020

(54) X-RAY DETECTOR WITH HEATING LAYER ON CONVERTER MATERIAL

(71) Applicant: Siemens Healthcare GmbH, Erlangen (DE)

(72) Inventors: Thorsten Ergler, Erlangen (DE); Miguel Labayen De Inza, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/022,913

(22) Filed: Jun. 29, 2018

(65) Prior Publication Data

US 2018/0321396 A1 Nov. 8, 2018

Related U.S. Application Data

(62) Division of application No. 15/364,390, filed on Nov. 30, 2016, now Pat. No. 10,156,644.

(30) Foreign Application Priority Data

Dec. 17, 2015 (DE) ........................ 10 2015 225 774

(51) Int. Cl.
*G01T 1/24* (2006.01)
*A61B 6/00* (2006.01)

(52) U.S. Cl.
CPC ............ *G01T 1/244* (2013.01); *A61B 6/4233* (2013.01); *A61B 6/4488* (2013.01); *G01T 1/241* (2013.01)

(58) Field of Classification Search
CPC ....... G01T 1/244; G01T 1/241; A61B 6/4488; A61B 6/4233
See application file for complete search history.

(56) References Cited

U.S. PATENT DOCUMENTS

| | | | |
|---|---|---|---|
| 6,037,595 A | 3/2000 | Lingren | |
| 7,256,402 B1 | 8/2007 | Lee | |
| 8,093,535 B2 | 1/2012 | Heismann et al. | |
| 9,547,091 B2 | 1/2017 | Ergler et al. | |
| 2002/0030239 A1 | 3/2002 | Der Ropp | |

(Continued)

FOREIGN PATENT DOCUMENTS

| DE | 10034262 C1 | 9/2001 |
|---|---|---|
| DE | 10138913 A1 | 3/2003 |

(Continued)

OTHER PUBLICATIONS

German Office Action thereof for DE 10 2015 225 774.6 dated Aug. 10, 2016.

*Primary Examiner* — Michael C Bryant
(74) *Attorney, Agent, or Firm* — Harness, Dickey & Pierce, P.L.C.

(57) ABSTRACT

A counting X-ray detector includes, in a stacked array, a converter material for converting X-ray radiation into electric charges and an electrode. In an embodiment, the electrode is electrically conductively connected to the converter material. The electrode is designed to be at least partly transparent. In an embodiment, the electrode includes: an electrically conductive contact layer, an electrically conductive first intermediate layer, an electrically conductive high voltage layer, a second intermediate layer and an electrically conductive heating layer.

25 Claims, 7 Drawing Sheets

(56) References Cited

U.S. PATENT DOCUMENTS

| | | |
|---|---|---|
| 2003/0016779 A1 | 1/2003 | Pohan et al. |
| 2003/0168605 A1 | 9/2003 | Chambaud et al. |
| 2007/0003006 A1 | 1/2007 | Tkaczyk et al. |
| 2008/0164418 A1 | 7/2008 | Shahar et al. |
| 2009/0026382 A1* | 1/2009 | Sakamoto ............ G01T 1/2928 250/370.09 |
| 2011/0186741 A1* | 8/2011 | Ohta ........................ G01T 1/24 250/370.08 |
| 2011/0311023 A1* | 12/2011 | Sagoh .................... A61B 6/032 378/19 |
| 2013/0040516 A1 | 2/2013 | Pruneri et al. |
| 2015/0260856 A1 | 9/2015 | Dierre et al. |
| 2017/0176608 A1* | 6/2017 | Ergler .................... G01T 1/241 |
| 2017/0192110 A1* | 7/2017 | Steadman Booker .. G01T 1/244 |
| 2017/0242135 A1 | 8/2017 | Ergler et al. |
| 2018/0088248 A1* | 3/2018 | Ergler ................... A61B 6/032 |

FOREIGN PATENT DOCUMENTS

| | | |
|---|---|---|
| DE | 102014207324 A1 | 10/2015 |
| WO | WO-20150158509 A1 | 10/2015 |
| WO | WO-2016046014 A1 | 3/2016 |

* cited by examiner

X-RAY DETECTOR WITH HEATING LAYER ON CONVERTER MATERIAL

PRIORITY STATEMENT

This application is a divisional application of and claims priority under 35 U.S.C. § 120/121 to U.S. application Ser. No. 15/364,390 filed Nov. 30, 2016, which claims priority under 35 U.S.C. § 119 to German patent application number DE 102015225774.6 filed Dec. 17, 2015, the entire contents of which are hereby incorporated herein by reference.

FIELD

At least one embodiment of the invention generally relates to a counting X-ray detector, a medical device and/or a method for regulating the temperature of a converter material in an X-ray detector.

BACKGROUND

In X-ray imaging, for example in computed tomography, angiography, or radiography, counting direct-converting X-ray detectors can be used. The X-ray radiation or the photons can be converted into electric pulses by an appropriate sensor. CdTe, CZT, CdZnTeSe, CdTeSe, CdMnTe, InP, $TlBr_2$, $HgI_2$, GaAs or others can be used, for example, as a converter material for the sensor.

The energy of the incident ionizing radiation is directly converted into electrical charges, known as electron-hole pairs. A high voltage, for example, for CdTe, CZT, CdZnTeSe, CdTeSe or CdMnTe in the region of −500 to −2000V, is applied to the converter material between an electrode serving as a cathode and a readout contact serving as an anode, in order to separate the charges of the electron-hole pairs triggered in the converter material. The high voltage is applied to the electrode via an external high voltage source by way of an electrically conductive contact.

The sensor is generally connected in a planar manner in a stacked array with a readout and/or an evaluation unit, for example, to an integrated circuit (an Application Specific Integrated Circuit, ASIC), via soldered connections, electrically conductive adhesive, or other methods. The electric pulses are evaluated by an evaluation unit, an ASIC for example. The stacked array comprising the sensor and the integrated circuit is connected to a further substrate, for example a printed circuit board, a ceramic substrate such as, for example, HTCC or LTCC, or others. The electrical connections for reading out from the readout and/or the evaluation unit can be designed as through connections (through-silicon via, TSV) or wire bonds.

DE 10 2012 213 410 B3 discloses a direct-converting X-ray radiation detector, which comprises at least one electrode mounted on a semiconductor. The at least one electrode and the semiconductor are electrically conductively connected, the at least one electrode being designed to be transparent and electrically conductive.

U.S. Pat. No. 8,093,535 B2 discloses a circuit incorporated in a semiconductor material in order to measure signals from the sensor assigned to the integrated circuit. In at least one embodiment, the circuit comprises an active component, a temperature sensor, and a circuit to control the temperature of the semiconductor material. The active component is designed to process measuring signals produced by the sensor. The active component is intended to be controlled by the circuit in an activatable manner around the temperature, such that the temperature of the semiconductor material is variable. The circuit further comprises at least one of a PI- and PID-regulator in order to control the temperature.

U. S. 2003/0168605 A1 discloses a radiation detector having at least one semi-conductive connection, the semi-conductive connection being designed to generate electron-hole pairs through the detection of radiation and the semi-conductive connection being wired in a photovoltaic mode of operation. The detector has means for operating and maintaining the connection at an almost constant temperature.

DE 100 34 262 C1 discloses a semiconductor device, wherein an integrated circuit runs dummy work cycles in order to generate heat if the temperature of the semiconductor device drops below a lower limiting value.

DE 101 38 913 A1 discloses a detector module for X-ray computer tomographs, wherein a sensor array comprising a plurality of sensor elements is mounted on the front of a printed circuit board. To increase the accuracy of the detector, provision is made according to the invention on the back of the printed circuit board, which faces away from the sensor array, for at least one heating element to be provided to heat the sensor array and for an electronic control unit arranged in the vicinity of the heating element to control the heating element.

SUMMARY

The inventors have identified a problem in that the availability of indium for the production of transparent electrodes comprising indium-containing TCO (Transparent Conductive Oxide) is limited and that the production costs in the TCO deposition process are relatively high. The inventors have further identified a problem in that the indirect heating of the converter material, using for example, heating elements in the evaluation unit or using heating elements on the underside of the evaluation unit do not provide adequate accuracy of temperature stabilization.

Embodiments of the invention include a counting X-ray detector, a medical device and a method for regulating the temperature of a converter material in an X-ray detector which allow an illumination of the converter material, the application of a high voltage to the converter material and optionally a regulation of the temperature of the converter material from a radiation incidence side.

Embodiments of the invention is directed to a counting X-ray detector of a first type, a counting X-ray detector of a next type, a medical device, and a method for regulating the temperature of a converter material of an X-ray detector.

At least one embodiment of the invention relates to a counting X-ray detector comprising, in a stacked array, a converter material for converting X-ray radiation into electrical charges, and an electrode. The electrode is electrically conductively connected to the converter material. The electrode is designed to be at least partly transparent. The electrode has the following layers: an electrically conductive contact layer, an electrically conductive first intermediate layer, an electrically conductive high voltage layer, a second intermediate layer, and an electrically conductive heating layer.

According to one embodiment of the invention, the electrode further comprises a first carrier protection layer and/or a second carrier protection layer.

According to one embodiment of the invention, the electrode further comprises a first carrier protection layer arranged in the region of the high voltage layer and/or a second carrier protection layer arranged in the region of the heating layer.

At least one embodiment of the invention further relates to a counting X-ray detector comprising, in a stacked array, a converter material for converting X-ray radiation into electrical charges and a further electrode. The further electrode is electrically connected to the converter material. The further electrode is designed to be at least partly transparent. The further electrode comprises the following layers: an electrically conductive contact layer, an electrically conductive first intermediate layer and an electrically conductive high voltage layer, which is designed in the shape of a mesh. The counting X-ray detector can further comprise a first carrier protection layer.

At least one embodiment of the invention further relates to a medical device comprising an X-ray detector according to at least one embodiment of the invention. The advantages of the X-ray detector according to embodiments of the invention that comprises the electrode can be transferred to the medical device according to embodiments of the invention.

At least one embodiment of the invention further relates to a method for regulating the temperature of a converter material of an X-ray detector according to the invention comprising:

determining a first temperature, comparing the first temperature with a predetermined second temperature value, and adjusting a current passing through an electrically conductive heating layer to regulate the temperature of the converter material. In the determination step, a first temperature is determined or measured, for example on the side of the readout and/or the evaluation unit that faces the converter material or in the readout and/or the evaluation unit. In the comparison step, the first temperature is compared with the predetermined second temperature, by means, for example, of a comparator in the readout and/or the evaluation unit. The second temperature can be a yardstick or a comparative value for a temperature in the converter material. In the adjustment step, the current passing through the electrically conductive heating layer for regulating the temperature or regulating the temperature of the converter material is adjusted.

BRIEF DESCRIPTION OF THE DRAWINGS

Example embodiments of the invention are described in greater detail hereinafter in connection with the drawings. The drawings show.

DETAILED DESCRIPTION OF THE EXAMPLE EMBODIMENTS

In the following, embodiments of the invention are described in detail with reference to the accompanying drawings. It is to be understood that the following description of the embodiments is given only for the purpose of illustration and is not to be taken in a limiting sense. It should be noted that the drawings are to be regarded as being schematic representations only, and elements in the drawings are not necessarily to scale with each other. Rather, the representation of the various elements is chosen such that their function and general purpose become apparent to a person skilled in the art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a counting X-ray detector comprising, in a stacked array, a converter material for converting X-ray radiation into electrical charges, and an electrode. The electrode is electrically conductively connected to the converter material. The electrode is designed to be at least partly transparent. The electrode has the following layers: an electrically conductive contact layer, an electrically conductive first intermediate layer, an electrically conductive high voltage layer, a second intermediate layer, and an electrically conductive heating layer.

The inventors have identified that a need exists for an electrode for an X-ray detector, which is transparent or has low absorption, for example to X-ray radiation, UV, IR or visible light, which at the same time is economical to produce and does not comprise any material that is rare or of limited availability. The inventors have further identified that the temperature stabilization via a heating layer in direct thermal connection with the converter material allows an accuracy of temperature of up to less than 1K or equal to 1K exactly. The inventors have identified that it is possible to stabilize the temperature with an electrode, to apply a high voltage to the converter material, and to design the electrode such that the converter material can be illuminated.

The X-ray detector may be a counting X-ray detector. The X-ray detector comprises a directly-converting converter material, for example CdTe, CZT, CdZnTeSe, CdTeSe, CdMnTe, InP, $TlBr_2$, $HgI_2$ or GaAs. The converter material and the readout or/and the electronic evaluation unit can be arranged in a stacked array. On the side of the converter material that faces away from the beam, at least one readout contact can be provided as an anode. The anode can be subdivided in a pixelated manner. On the side of the converter material that faces the beam, an electrode is provided as a cathode. The electrode is planar in design. A sensor can comprise the converter material, the electrode and the anode.

The electrode and the converter material may be arranged in a stacked array. The electrode and the converter material can be electrically connected to each other in a planar manner. The electrode and the converter material can at least approximately have the same planar extent.

The electrode may be designed to be at least partly transparent. The electrode can be at least partly transparent to or have low absorption of, for example UV, IR or visible light. Preferably the electrode can be at least partly transparent to or have low absorption of, for example, X-ray radiation and IR light. The electrode can be designed to be at least partly transparent to UV, IR or visible light, such that a maximum of 30 percent of the irradiated UV, IR or visible light can be absorbed. The electrode can be at least partly electrically conductive.

The electrode comprises a plurality of layers in a stacked array. The layers can be connected to each other in a planar manner. The electrode can comprise the following layers in the following sequence: the electrically conductive contact layer, the electrically conductive first intermediate layer, the electrically conductive high voltage layer, the second intermediate layer, and the electrically conductive heating layer.

The contact layer can be electrically conductively connected directly to the converter material. The contact layer can be applied directly onto the converter material. The first intermediate layer can be applied directly onto the contact layer. The high voltage layer can be applied directly onto the first intermediate layer. The second intermediate layer can be applied directly onto the high voltage layer. The heating layer can be applied directly onto the second intermediate layer. Applying can be understood as deposition, vapor deposition, adhesive bonding, applying, mounting, brushing or other methods for applying coatings.

The properties of the converter material for the detection of ionizing radiation, of X-ray radiation for example, can be optimized by additional irradiation of IR, UV or visible light, for example from the side that faces towards the beam. The electrode can be at least partly transparent to IR, UV, or visible light and the X-ray detector can advantageously be optimized via additional irradiation of IR, UV, or visible light.

The electrically conductive contact layer can be a thin metallic layer, comprising for example, platinum, indium, molybdenum, tungsten, ruthenium, rhodium, gold, silver or aluminum. The electrically conductive contact layer can be a thin metallic layer. The contact layer can be designed to be at least partly transparent. The contact layer can have a thickness of a maximum of 250 nm, preferably a maximum of 200 nm, and particularly preferably a maximum of 150 nm. The contact layer can be designed to be porous, the pores in the contact layer being transparent to electromagnetic radiation, in particular to IR and X-ray radiation. The contact layer can be designed in the form of a mesh.

The electrically conductive first intermediate layer can be designed to be at least partly transparent. The first intermediate layer can be an electrically conductive adhesive tape. The electrically conductive first intermediate layer can comprise an electrically conductive adhesive. The electrically conductive first intermediate layer can comprise a bonding agent and at least one electrically conductive filler element embedded therein. The bonding agent can be designed to be at least partly transparent or semi-transparent, preferably transparent, to electromagnetic radiation, in particular to X-ray radiation and IR light. The filler element can form an electrically conductive connection between the contact layer and the high voltage layer. The filler element can be designed from a metal. The first intermediate layer can have a degree of absorption of 75 percent maximum, preferably 60 percent maximum, particularly preferably 50 percent maximum and in most cases preferably have a maximum of 40 percent of the intensity of IR, UV, or visible light.

The electrically conductive high voltage layer can be designed as a TCO layer. The TCO layer can be designed from at least one material in the list that follows: indium tin oxide, indium oxide, tin oxide, zinc oxide, cadmium oxide, poly 3,4-ethylene dioxythiophene, polystyrene sulfonate, carbon nanotubes or polyaniline derivatives. The TCO layer can be designed from at least one pure or a doped material.

The electrically conductive high voltage layer can be designed in the form of a mesh. The electrically conductive high voltage layer can be designed as an electrically conductive mesh, in particular as a metallic mesh. The electrically conductive mesh can comprise copper, silver, nickel, gold or suchlike. The electrically conductive mesh can be designed to be so thin that the electrically conductive mesh is transparent to X-ray radiation. The electrically conductive mesh, in particular the crosspieces of the electrically conductive mesh, can be designed such that the mesh is not transparent to UV, IR, or visible light. The electrically conductive mesh can be designed to be at least partly transparent to UV, IR, or visible light, such that a maximum of 30 percent of the irradiated UV, IR, or visible light is absorbed. The electrode can be designed to be at least partly transparent to UV, IR, or visible light, such that a maximum of 30 percent of the irradiation of UV, IR, or visible light is absorbed. The electrically conductive mesh can form a regular or an irregular pattern. The spaces between the crosspieces of the mesh can be small enough for sufficient filler elements in the first intermediate layer to have an electrically conductive contact with the electrically conductive mesh.

Advantageously, the electrically conductive mesh can be more economical in production than the deposition of TCO layers. Advantageously, the production of an electrode comprising an electrically conductive mesh can be more economical than the production of an electrode comprising a TCO layer.

The second intermediate layer can be electrically conductive. The second intermediate layer can be electrically insulating or non-conductive. The second intermediate layer can preferably be electrically insulating. The second intermediate layer can be an adhesive strip or comprise an adhesive. The second intermediate layer can be similar in design to the first intermediate layer. The second intermediate layer can comprise a bonding agent. The second intermediate layer can comprise at least one electrically conductive filler element embedded in the bonding agent.

The electrically conductive heating layer can be designed as a TCO layer or as an electrically conductive mesh. Due to its electrical resistance, the heating layer can be used as a heating element, in that the electric current passing through the heating layer is monitored or controlled or regulated. To regulate the electric current through the heating layer, a first temperature measured on the surface of the readout and/or the evaluation unit, for example on an integrated circuit (an Application Specific Integrated Circuit, ASIC), can be used. The first temperature can be compared with a predetermined second temperature. The comparison of the first temperature with the second temperature can be carried out in a comparator in the readout and/or the evaluation unit, for example in an integrated circuit (an Application Specific Integrated Circuit, ASIC).

In the event of a first temperature that is lower compared to the second temperature, the electric current or current flow through the heating layer can be increased. In the event of a first temperature that is higher compared to the second temperature, the electric current or current flow through the heating layer can be reduced. In the event of a first temperature that is the same compared to the second temperature, the electric current or current flow through the heating layer can be increased or reduced or maintained at a constant value depending on the design of the comparator. A plurality of heating layers can be arranged such that they are spatially separated from one another inside the electrode, it being possible to regulate the currents passing through the heating layers by using different electric circuits or a shared electric circuit. A plurality of electrodes can be arranged on the converter material, it being possible, for example, for the currents passing through the heating layers to be regulated using different electric circuits or a shared electric circuit.

The electrical resistance of the converter material can change with the flow of the incident ionizing radiation. The electric current in the converter material can change with the flow of the incident ionizing radiation. As a result thereof, the dissipation and the temperature of the converter material can change. The change in the temperature in the converter material can lead to a change in the count rate or/and the energy resolution of the X-ray detector. As a result thereof, unwanted artifacts can be caused in the reconstructed image. A high degree of thermal stability is therefore desirable.

Advantageously, the heat flow can ensue from the side facing the beam. Advantageously, the heat flow can emanate from a heating element in direct thermal contact with the converter material. Advantageously, a particularly regular heating of the converter material is possible. Advantageously, the heat flow can emanate from a heating element encompassed by the electrode. Advantageously, the heat flow or the heat can spread in the converter material. Advantageously, a homogeneous temperature or temperature distribution can be achieved in the converter material. Advantageously, the heat flow can spread from the converter material across the soldered or electrically conductive adhesive bond to the readout- and/or the evaluation unit, for example to an integrated circuit (an Application Specific Integrated Circuit, ASIC), and further spread to the further substrate. Advantageously, the heat flow emanating from the heating layer can be used more effectively to regulate the temperature of the converter material than a heat flow that emanates from heating elements in the further substrate, on the side of the further substrate that faces away from the beam or in the readout and/or the evaluation unit.

Advantageously, the thermal management or the heat flow can be simplified as compared with the disadvantageous array of heating elements or cooling elements in the further substrate, on the side of the further substrate that faces away from the beam, or in the readout and/or the evaluation unit. Advantageously, an improved temperature stability can be achieved since, due to the direct array of the electrode comprising the heating layer, the chronologically fast rapid temperature changes, which are typical, of computer tomography for example, can be counteracted. The heat flow that emanates from heating elements or cooling elements in the further substrate, on the side of the further substrate that faces away from the beam or in the readout and/or the evaluation unit can be chronologically more slowly pronounced than the heat flow emanating from the electrode comprising the heating layer. Advantageously, a temperature stability of 1K or less can be achieved in the converter material.

According to one embodiment of the invention, the electrode further comprises a first carrier protection layer and/or a second carrier protection layer.

According to one embodiment of the invention, the electrode further comprises a first carrier protection layer arranged in the region of the high voltage layer and/or a second carrier protection layer arranged in the region of the heating layer.

The electrode can comprise the following layers in the following sequence: the electrically conductive contact layer, the electrically conductive first intermediate layer, the electrically conductive high voltage layer, the first carrier protection layer, the second intermediate layer, the electrically conductive heating layer, and the second carrier protection layer. The contact layer can be electrically conductively connected directly to the converter material. The contact layer can be applied directly onto the converter material. The first intermediate layer can be applied directly onto the contact layer. The high voltage layer can be applied directly onto the first intermediate layer. The first carrier protection layer can be applied directly onto the high voltage layer. The second intermediate layer can be applied directly onto the first carrier protection layer or onto the high voltage layer. The heating layer can be applied directly onto the second intermediate layer. The second carrier protection layer can be applied directly onto the heating layer.

The first carrier protection layer and/or the second carrier protection layer can be a carrier foil. The first carrier protection layer and/or the second carrier protection layer can be designed, for example, from polyethylene terephthalate, polyethylene terephthalate glycols, polypropylene, polyethylene, polyvinyl chloride or suchlike. The first carrier protection layer and/or the second carrier protection layer can be designed to be electrically insulating or non-conductive.

According to one embodiment of the invention, an electric circuit is provided to apply a current to the electrically conductive heating layer as a function of a first temperature that is acquired in the X-ray detector.

The electric circuit can be provided in the readout and/or the evaluation unit, on the further substrate, inside or outside the X-ray detector. The electric circuit can preferably be provided in the evaluation and/or readout unit or in the electrode. The current can be regulated as a function of the first temperature. The current can be regulated as a function of the result of the comparison in a comparator. A current can be applied to the heating layer. The circuit can be provided for any X-ray detector.

Advantageously, the current can be regulated as a function of the first temperature. Advantageously, the current can be applied to the converter material for any X-ray detector, irrespective of further X-ray detectors.

According to one embodiment of the invention, the electrically conductive high voltage layer or the electrically conductive heating layer is designed as an electrically conductive mesh, in particular as a metallic mesh. Advantageously, the electrically conductive mesh can be more economical in production than the deposition of TCO layers. Advantageously, the production of an electrode comprising an electrically conductive mesh can be more economical than the production of an electrode comprising a TCO layer.

According to one embodiment of the invention, the electrically conductive high voltage layer or the electrically conductive heating layer is designed as a TCO layer. Advantageously, the TCO layer can be homogeneously transparent in a planar manner or slightly absorbent. Advantageously, the electrically conductive connection to the first intermediate layer can be produced reliably in a planar manner.

According to one embodiment of the invention, the X-ray detector comprises a temperature sensor to acquire the first temperature on a side of the converter material that faces away from the electrode. The temperature sensor can be encompassed by the readout and/or the evaluation unit or the further substrate. The temperature sensor can be configured on the side of, on top of, in, or under the readout and/or the evaluation unit or the further substrate. The temperature sensor can be designed to be between the converter material and the readout and/or the evaluation unit. The temperature sensor can be designed to be in direct thermal connection with the converter material. The temperature sensor can be arranged directly on the converter material. A temperature diode can be provided as a temperature sensor in the electrode, the signal from which can be evaluated outside the electrode. Advantageously, the temperature sensor can determine a first temperature. The temperature sensor can determine the first temperature in its position or its location. The first temperature can represent, for example, a temperature on the side of the readout and/or the evaluation unit that faces towards the converter material or in the electrode. Advantageously, the first temperature can represent a yardstick for the temperature of the converter material.

According to one embodiment of the invention, the X-ray detector further comprises a comparator to compare the first temperature with a predeterminable second temperature value. Advantageously, the first temperature can be compared with a predetermined second temperature value in the X-ray detector. Advantageously, the comparison of the temperature can be carried out for each X-ray detector irrespective of further X-ray detectors.

According to one embodiment of the invention, the converter material comprises the element cadmium. Advantageously, the converter material can comprise suitable or optimal absorption properties for medical imaging, in particular with a computer tomograph.

According to one embodiment of the invention, the electrically conductive mesh comprises at least one of the following elements: copper, silver, nickel, or gold. Advantageously, the electrically conductive mesh can be suitable for applying a high voltage. Advantageously, the electrically conductive mesh can be suitable for applying a current. Advantageously, the electrically conductive mesh can comprise a suitable electrical resistance to heat the converter material. Advantageously, the electrically conductive mesh can be produced by known and economical methods.

According to one embodiment of the invention, the X-ray detector further comprises an illumination device to illuminate the converter material. The X-ray detector can include an illumination device for illumination or for additional irradiation. The medical device can include an illumination device for illumination or for additional irradiation. The illumination or the additional irradiation can include the illumination with a UV or IR light source or a light source for visible light. The illumination device can for example be designed as a light conductor or diffusor, into which UV, IR, or visible light can be injected.

According to one embodiment of the invention, the electrically conductive mesh absorbs less than 30 percent of the amount of light that is beamed onto the converter material by the illumination device. The amount of light can relate to the amount of UV, IR, or visible light. Advantageously, the properties of the converter material can be optimized by the additional irradiation or illumination.

According to one embodiment of the invention, the contact layer comprises one of the following elements: platinum, indium, molybdenum, tungsten, ruthenium, rhodium, gold, silver or aluminum. Advantageously, the contact layer can be suitable for forming an electrically conductive connection. Advantageously, the high voltage can be applied to the converter material via the contact layer.

According to one embodiment of the invention, the contact layer is designed to be at least partly transparent. The contact layer can be designed to be at least partly transparent to UV, IR, or visible light. The contact layer can be designed to be at least partly transparent to ionizing radiation, for example, to X-ray radiation. The contact layer can preferably be transparent or have low absorption to ionizing radiation. Advantageously, the influence of the contact layer on the imaging properties can be slight or negligible. Advantageously, the contact layer can allow an additional irradiation of the converter material with UV, IR, or visible light in order to optimize the imaging.

According to one embodiment of the invention, the electrically conductive first intermediate layer comprises an bonding agent and an electrically conductive filler. The second intermediate layer can be designed in a similar manner to the first intermediate layer. Advantageously, the first intermediate layer can be used to affix the high voltage layer. Advantageously, the first intermediate layer can form an electrically conductive connection between the high voltage layer and the contact layer.

According to one embodiment of the invention, an electrically conductive connection is configured between the electrode and a voltage source. An electrically conductive connection can be configured between an external voltage source and the electrode or the further electrode. Advantageously, a high voltage can be applied to the electrode and hence to the converter material.

According to one embodiment of the invention, the electrically conductive connection includes a continuation of the electrically conductive high voltage layer. The electrically conductive connection can be configured as a continuation of the high voltage layer. The electrically conductive connection can include the first carrier protection layer. The continuation of the high voltage layer can be partly or completely covered by the first carrier protection layer. Advantageously, the first carrier protection layer can comprise an electrically insulating or mechanically supportive function. Advantageously, the voltage source can be connected to a connection point, by for example a soldered connection, or by few connection points with the high voltage layer. Advantageously, an appropriate mechanical stability of the electrically conductive connection between the voltage source and the electrode or the high voltage layer can be guaranteed. The electrically conductive connection between the power source and the heating layer can be configured as a continuation of the electrically conductive heating layer.

At least one embodiment of the invention further relates to a counting X-ray detector comprising, in a stacked array, a converter material for converting X-ray radiation into electrical charges and a further electrode. The further electrode is electrically connected to the converter material. The further electrode is designed to be at least partly transparent. The further electrode comprises the following layers: an electrically conductive contact layer, an electrically conductive first intermediate layer and an electrically conductive high voltage layer, which is designed in the shape of a mesh. The counting X-ray detector can further comprise a first carrier protection layer.

On the side of the converter material that faces the beam, the further electrode is provided as a cathode. The further electrode is planar in design. A sensor can include the converter material, the further electrode and the anode. The further electrode and the converter material are arranged in a stacked array. The further electrode and the converter material are electrically connected to each other over a broad area. The further electrode and the converter material can at least approximately have the same planar expanse.

The further electrode is designed to be at least partly transparent. The further electrode can be at least partly transparent or have low absorption, for example to X-ray radiation, UV, IR, or visible light. The further electrode can be at least partly transparent or have low absorption to X-ray radiation and IR light. The further electrode is at least partly transparent to IR, UV, or visible light and the properties of the converter material can be optimized advantageously by additional irradiation of IR, UV, or visible light. The further electrode can be designed to be at least partly transparent to UV, IR, or visible light, such that a maximum of 30 percent of the irradiation of UV, IR, or visible light can be absorbed. The further electrode can be at least partly electrically conductive. The further electrode comprises a plurality of layers in a stacked array. The layers are connected to each other in a planar manner. The further electrode can comprise the following layers in the following sequence: the electrically conductive contact layer, the electrically conductive first intermediate layer, the electrically conductive high voltage layer, and the first carrier protection layer. The contact layer can be electrically conductively connected directly to the converter material. The contact layer can be applied directly on the converter material. The first intermediate layer can be applied directly on the contact layer. The high voltage layer can be applied directly onto the first intermediate layer. The first carrier protection layer can be applied directly onto the high voltage layer.

The electrically conductive high voltage layer in the further electrode is designed in the form of a mesh. The high voltage layer can be an electrically conductive mesh. Advantageously, the production of an electrode comprising an electrically conductive mesh can be more economical than the production of an electrode comprising a TCO layer.

At least one embodiment of the invention further relates to a medical device comprising an X-ray detector according to at least one embodiment of the invention. The advantages of the X-ray detector according to embodiments of the invention that comprises the electrode can be transferred to the medical device according to embodiments of the invention.

Advantageously, unwanted artifacts in the reconstructed image can be reduced by the high thermal stability of 1K or less. The properties of the converter material can be optimized via additional irradiation of IR, UV, or visible light onto the converter material, such that the imaging is advantageously improved.

The advantages of embodiments of the X-ray detector comprising the further electrode can be transferred to embodiments of the medical device according to the invention. Advantageously, the quality of the imaging can be optimized via additional irradiation of IR, UV, or visible light onto the converter material.

At least one embodiment of the invention further relates to a method for regulating the temperature of a converter material of an X-ray detector according to the invention comprising:

determining a first temperature, comparing the first temperature with a predetermined second temperature value, and adjusting a current passing through an electrically conductive heating layer to regulate the temperature of the converter material. In the determination step, a first temperature is determined or measured, for example on the side of the readout and/or the evaluation unit that faces the converter material or in the readout and/or the evaluation unit. In the comparison step, the first temperature is compared with the predetermined second temperature, by means, for example, of a comparator in the readout and/or the evaluation unit. The second temperature can be a yardstick or a comparative value for a temperature in the converter material. In the adjustment step, the current passing through the electrically conductive heating layer for regulating the temperature or regulating the temperature of the converter material is adjusted.

Advantageously, the temperature in the converter material can be controlled, adjusted or regulated.

Figure 1:
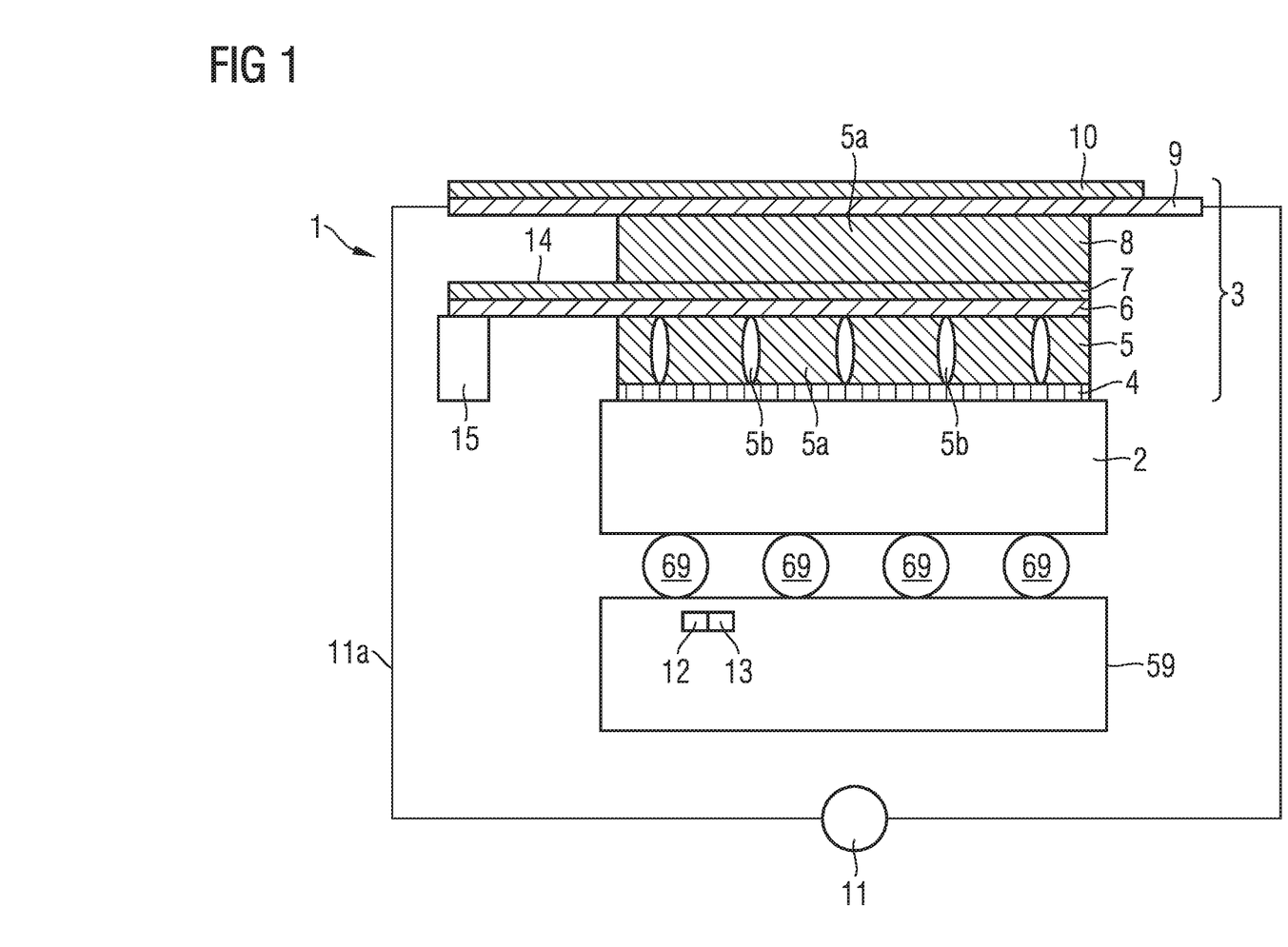
FIG. 1 in diagram form, is a concept for an X-ray detector according to a first embodiment.

FIG. 1 shows by way of example an embodiment of the X-ray detector 1 as per the invention according to a first embodiment. The counting X-ray detector 1 comprises in a stacked array a converter material 2 for converting X-ray radiation into electric charges, and an electrode 3. The electrode 3 is electrically conductively connected to the converter material 2. The electrode 3 and the converter material 2 are arranged in a stacked array. The electrode 3 and the converter material 2 are electrically connected to one another in a planar manner. The electrode 3 and the converter material 2 have at least approximately the same planar expanse. The electrode 3 is designed to be at least partly transparent. The electrode 3 is at least partly transparent or has low absorption, for example to X-ray radiation, UV, IR, or visible light. The electrode 3 is preferably at least partly transparent or has low absorption to X-ray radiation and IR light. The electrode 3 is designed to be at least partly transparent to UV, IR, or visible light such that a maximum of 30 percent of the irradiation of UV, IR, or visible light is absorbed. The properties of the converter material 2 for the detection of X-ray radiation are optimized by additional irradiation of IR, UV, or visible light from the side that faces the beam. The electrode 3 is at least partly electrically conductive.

The electrode 3 comprises a plurality of layers in a stacked array. The electrode 3 comprises the following layers in the following sequence: an electrically conductive contact layer 4, an electrically conductive first intermediate layer 5, an electrically conductive high voltage layer 6, a first carrier protection layer 7, a second intermediate layer 8, an electrically conductive heating layer 9, and a second carrier protection layer 10. The contact layer 4 is electrically conductively connected directly to the converter material 2. The contact layer 4 is applied directly onto the converter material 2. The first intermediate layer 5 is applied directly onto the contact layer 4. The high voltage layer 6 is applied directly onto the first intermediate layer 5. The first carrier protection layer 7 is applied directly onto the high voltage layer 6. The second intermediate layer 8 is applied directly onto the first carrier protection layer 7. The heating layer 9 is applied directly onto the second intermediate layer 8. The second carrier protection layer 10 is applied directly onto the heating layer 9. Applying can be understood as deposition, vapor deposition, adhesive bonding, applying, mounting, brushing or other methods for applying layers.

On the side that faces the beam, the converter material 2 comprises soldered connections 69, in order to form an electrically conductive connection to the readout and/or evaluation unit 59. The readout and/or the evaluation unit 59 have/has a temperature sensor 12 and a comparator 13. The electrically conductive connection 14 to the voltage source 15 is a continuation of the high voltage layer 6 and of the first carrier protection layer 7. The voltage source 15 and the electrically conductive connection 14 or the high voltage layer 6 are connected, for example, via a soldered connection, an indirect connection, a plug connection or an electrically conductive bond.

The electrically conductive contact layer 4 is a thin metallic layer, comprising, for example, platinum, indium, molybdenum, tungsten, ruthenium, rhodium, gold, silver or aluminum. The electrically conductive contact layer 4 is a thin foil layer. The contact layer 4 is designed to be at least partly transparent. The contact layer 4 has a thickness of a maximum of 250 nm, preferably a maximum of 200 nm, particularly preferably a maximum of 150 nm. The contact layer 4 can be designed to be porous, the pores in the contact layer 4 being transparent to electromagnetic radiation, in particular to IR and X-ray radiation. The contact layer 4 can alternatively be designed in the form of a network.

The electrically conductive first intermediate layer 5 is designed to be at least partly transparent. The first intermediate layer 5 is an electrically conductive adhesive strip or comprises an electrically conductive adhesive. The electrically conductive first intermediate layer 5 comprises a bonding agent 5a and at least one electrically conductive filler element 5b embedded therein. The bonding agent 5a is at least semi-transparent, preferably transparent, to electromagnetic radiation, in particular to X-ray radiation and IR light. The filler element 5b forms an electrically conductive connection between the contact layer 4 and the high voltage layer 6. The filler element 5b is designed from a metal. The first intermediate layer 5 has a maximum degree of absorption of 75 percent, preferably a maximum of 60 percent, particularly preferably a maximum of 50 percent, and most preferably a maximum of 40 percent of the intensity of IR, UV, or visible light.

The electrically conductive high voltage layer 6 is configured as a TCO layer or in the form of a mesh. The TCO layer can be designed from at least one material in the following list: indium tin oxide, indium oxide, tin oxide, zinc oxide, cadmium oxide, poly 3,4-ethylene dioxythiophene, polystyrene sulfonate, carbon nanotubes or polyaniline derivatives. The TCO layer can be designed from at least one pure or a doped material. The electrically conductive high voltage layer 6 can be designed in the form of an electrically conductive mesh 16. The electrically conductive mesh 16 can comprise copper, silver, nickel, gold or suchlike. The electrically conductive mesh 16 can be designed to be so thin that the electrically conductive mesh 16 is transparent to X-ray radiation. The electrically conductive mesh 16 can be designed such that it is not transparent to UV, IR, or visible light. The electrically conductive mesh 16 can be designed to be at least partly transparent to UV, IR, or visible light, such that a maximum of 30 percent of the irradiation of UV, IR, or visible light is absorbed. The electrically conductive mesh 16 can form a regular or an irregular pattern. The spaces between the crosspieces of the electrically conductive mesh 16 can be small enough for sufficient filler elements 5b in the first intermediate layer 5 to have an electrically conductive contact with the electrically conductive mesh 16.

At least the spaces between the crosspieces of the electrically conductive mesh 16 can be designed to be transparent.

The first carrier protection layer 7 is a carrier foil. The first carrier protection layer 7 and/or the second carrier protection layer 10 are/is designed, for example, from polyethylene terephthalate, polyethylene terephthalate glycols, polypropylene, polyethylene, polyvinyl chloride or suchlike. The first carrier protection layer 7 and/or the second carrier protection layer 10 are/is designed to be electrically insulating or non-conductive.

The second intermediate layer 8 can be electrically conductive or electrically insulating or non-conductive. The second intermediate layer 8 is an adhesive strip or comprises an adhesive. The second intermediate layer 8 can be designed like the first intermediate layer; for example, it can have the same bonding agent 5a or the same thickness as the first intermediate layer 5. The second intermediate layer 8 comprises a bonding agent 5a. The second intermediate layer 8, if it is designed to be electrically conductive, can comprise at least one electrically conductive filler element 5b embedded in the bonding agent 5a.

The electrically conductive heating layer 9 is designed as a TCO layer or as an electrically conductive mesh 16. The heating layer 9 is connected to a power source 11 via a further electrically conductive connection 11a. The further electrically conductive connection 11a to the power source 11 is electrically connected to a continuation of the heating layer 9. The power source 11 or the electrically conductive connection 11a and the continuation of the heating layer 9 are connected, for example, via a soldered connection, an indirect connection, a plug connection or an electrically conductive bond. Due to its electrical resistance, the heating layer 9 is used as a heating element, in that the electric current passing through the heating layer 9 is monitored or controlled or regulated.

To regulate the electric current passing through the heating layer 9, a first temperature measured on the surface of the readout and/or the evaluation unit 59, for example on an integrated circuit (an Application Specific Integrated Circuit, ASIC), is used. The first temperature is compared with a predetermined second temperature. There is a connection between the comparator 13 and the power source 11. The current flow or the power source 11 is controlled via a signal based on the output signal from the comparator 13. The output signal from the comparator 13 can be read off by way of a data readout from the readout and/or the evaluation unit 59. The signal based on the output signal from the comparator 13 can be processed using a further evaluation unit and used to control the current flow or the power source 11. The current can be applied to the heating layer 9 via an electric circuit.

The comparison of the first temperature with the second temperature is carried out in a comparator 13 in the readout and/or the evaluation unit 59, for example in an integrated circuit (an Application Specific Integrated Circuit, ASIC). In the event of a first temperature that is lower compared to the second temperature, the electric current or current flow through the heating layer 9 is increased. In the event of a first temperature that is higher compared to the second temperature, the electric current or current flow through the heating layer 9 is reduced. In the event of a first temperature that is the same compared to the second temperature, the electric current or current flow through the heating layer 9 can be increased or reduced or maintained at a constant value, depending on the design of the comparator 13.

In a further embodiment (not shown), the electrode comprises at least the following layers: an electrically conductive contact layer 4, an electrically conductive first intermediate layer 5, an electrically conductive high voltage layer 6, a second intermediate layer 8, and an electrically conductive heating layer 9. The second intermediate layer 8 is applied directly onto the high voltage layer 6. The second intermediate layer 8 is electrically insulating.

Figure 2:
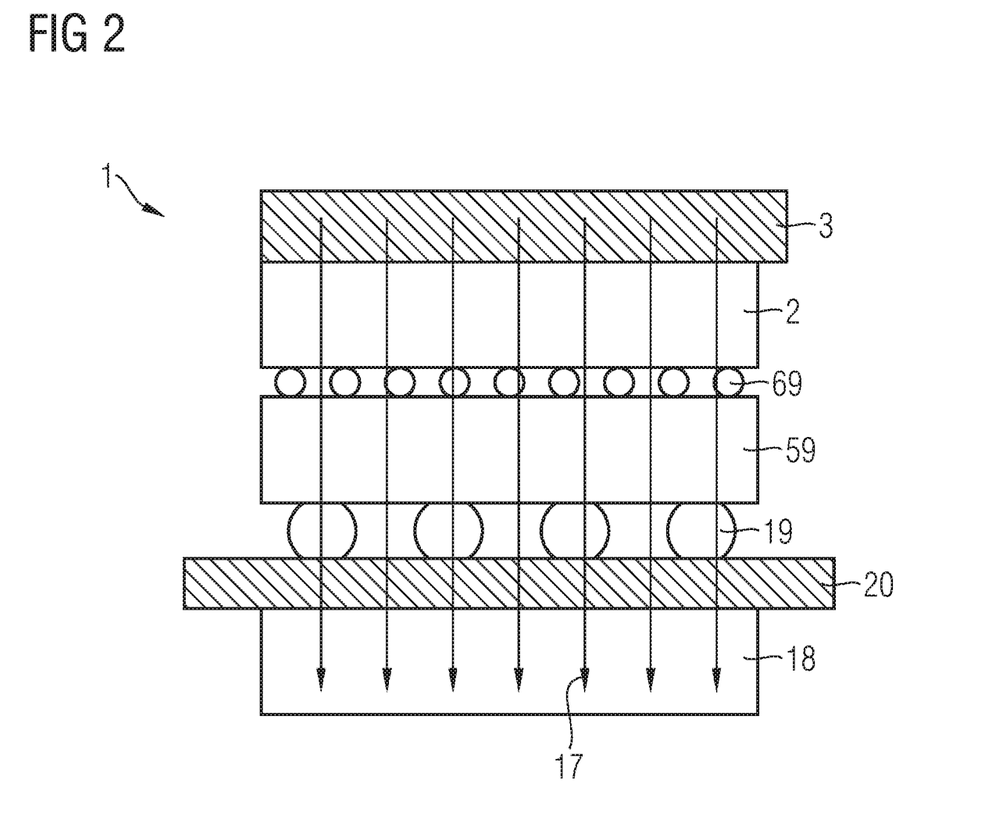
FIG. 2 in diagram form, is a concept for an X-ray detector according to a second embodiment.

FIG. 2 shows, by way of example, an embodiment of the X-ray detector 1 according to the invention as per a second embodiment. The heat flow 17 to the converter material 2 ensues from the side of the converter material 2 that faces the beam. The heat flow 17 emanates from the heating layer 9 encompassed by the electrode 3, in direct thermal contact with the converter material 2. The heat flow 17 or the heat can spread directly in the converter material 2. A homogeneous temperature or temperature distribution will be achieved in the converter material 2. The heat flow 17 spreads from the converter material 2 across the soldered connections 69 or electrically conductive adhesive bond to the readout and/or the evaluation unit 59, for example an integrated circuit (Application Specific Integrated Circuit, ASIC), and to the further substrate 18. The heat flow 17 emanating from the heating layer 9 is used more effectively to regulate the temperature of the converter material 2 than a heat flow 17 that emanates from heating elements in the further substrate 18, on the side of the further substrate 18 that faces away from the beam or in the readout and/or the evaluation unit 59.

An improved temperature stability is achieved since, due to the direct array of the electrode 3 comprising the heating layer 9, the chronologically rapid temperature changes, which are typical, for example, of computed tomography, are counteracted. The heat flow 17 that emanates from heating elements or cooling elements in the further substrate 18, on the side of the further substrate 18 that faces away from the beam or in the readout and/or the evaluation unit 59 can be chronologically more slowly pronounced than the heat flow 17 that emanates from the electrode 3 comprising the heating layer 9. A temperature stability of 1K or less is achieved in the converter material 2.

Figure 3:
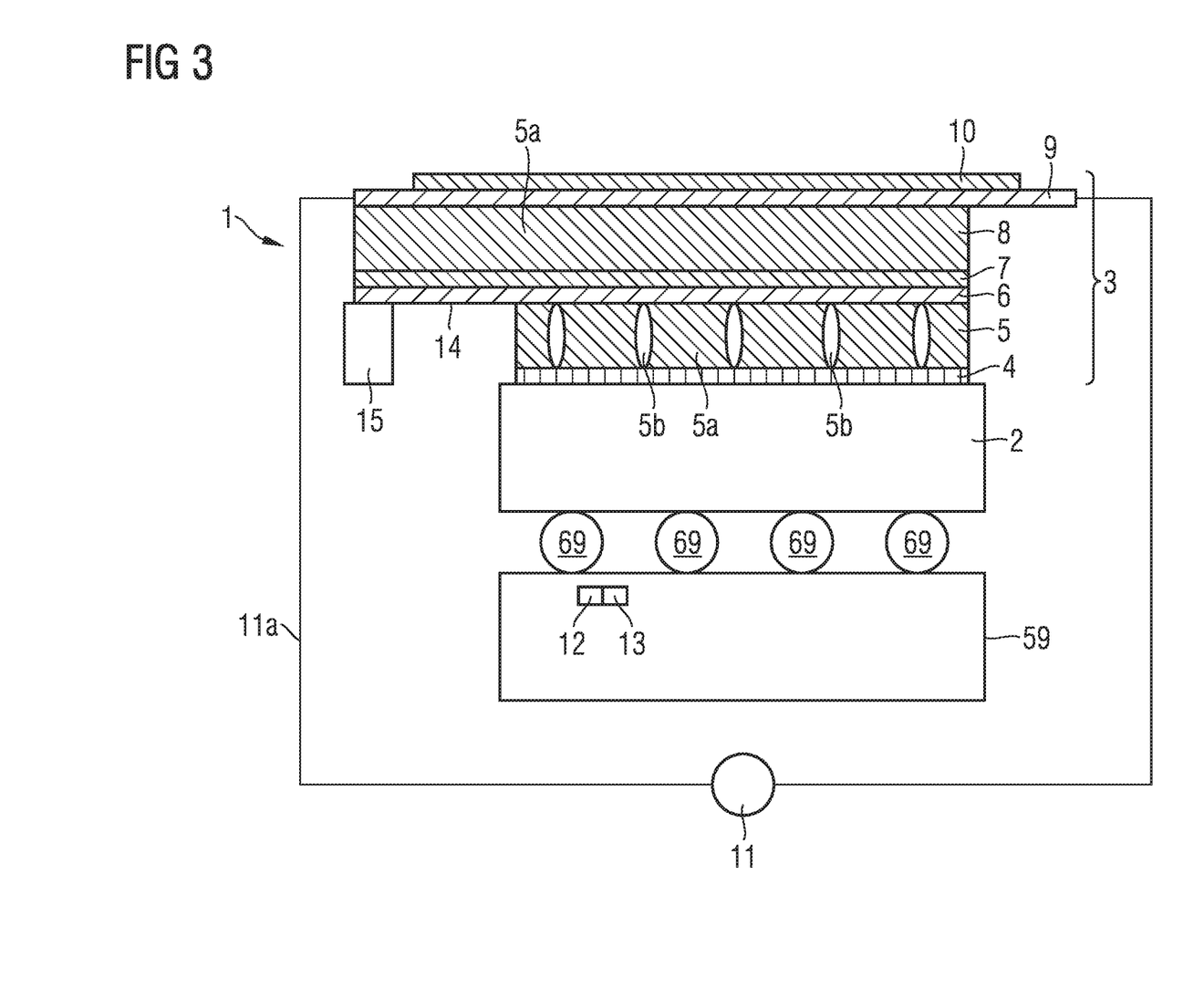
FIG. 3 in diagram form, is a concept for an X-ray detector according to a third embodiment.

FIG. 3 shows, by way of example, an embodiment of the X-ray detector according to the invention 1 as per a third embodiment. The electrically conductive connection 14 to the voltage source 15 and the further electrically conductive connection 11a to the power source 11 are a shared continuation of the high voltage layer 6, of the first carrier protection layer 7, of the second intermediate layer 8, of the heating layer 9 and of the second carrier protection layer 10.

Figure 4:
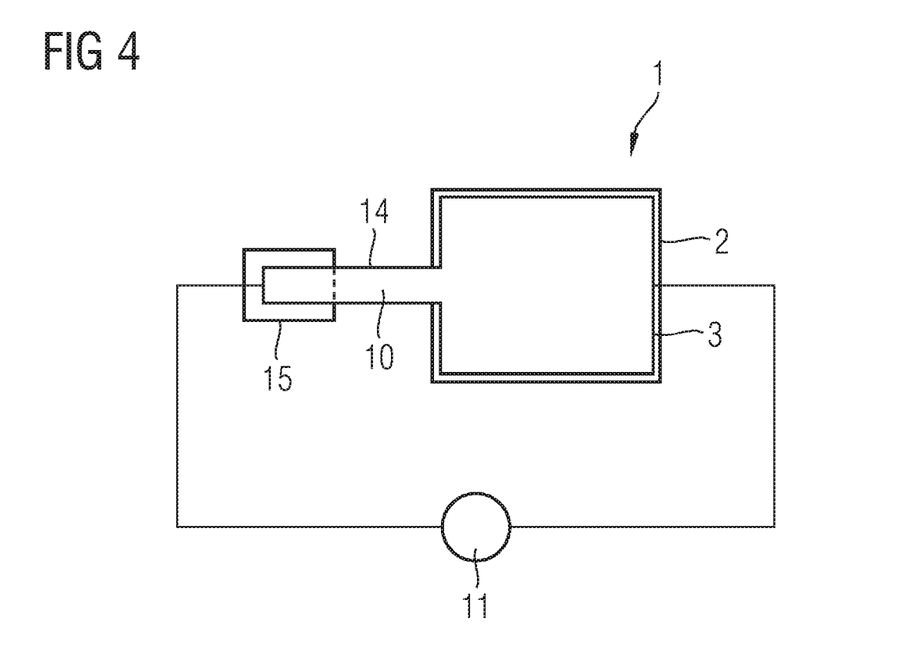
FIG. 4 in diagram form, is a concept for an X-ray detector according to a fourth embodiment.

FIG. 4 shows, by way of example, an embodiment of an X-ray detector 1 according to the invention as per a fourth embodiment. A view is shown onto the side of the X-ray detector 1 that faces the beam. The shared continuation of the high voltage layer 6, of the first carrier protection layer 7, of the second intermediate layer 8, of the heating layer 9 and of the second carrier protection layer 10 has a smaller width than the side of the electrode 3 that faces the voltage source 15.

Figure 5:
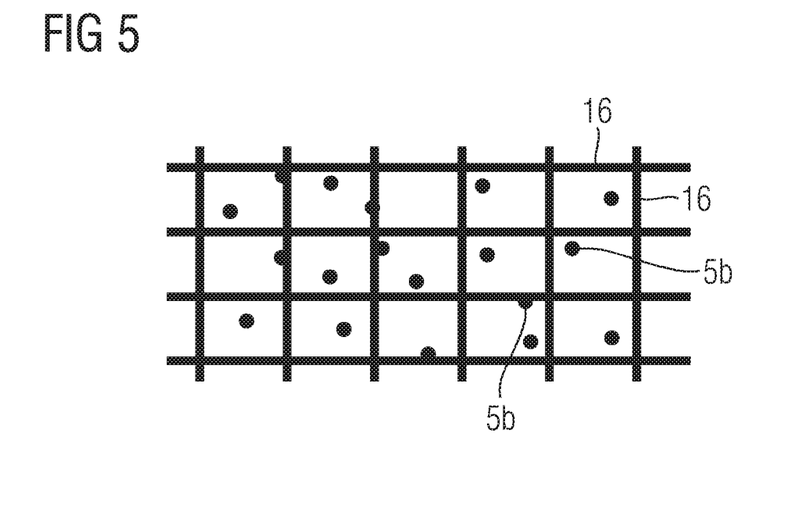
FIG. 5 in diagram form, is a concept for an electrically conductive mesh according to an embodiment of the invention.

FIG. 5 shows, by way of example, an embodiment of an electrically conductive mesh 16 according to the invention. The electrically conductive mesh 16 comprises at least one of the following metals: copper, silver, nickel, gold or suchlike. The electrically conductive mesh 16 can be designed to be so thin that the electrically conductive mesh 16 is transparent to X-ray radiation. The electrically conductive mesh 16 is designed to be at least partly transparent to UV, IR, or visible light, such that a maximum of 30 percent of the irradiation of UV, IR, or visible light is absorbed. The electrically conductive mesh 16 can form a regular or an irregular pattern. The spaces between the crosspieces of the electrically conductive mesh 16 can be small enough for sufficient filler elements 5b in the first intermediate layer 5 to have an electrically conductive contact with the electrically conductive mesh 6.

Figure 6:
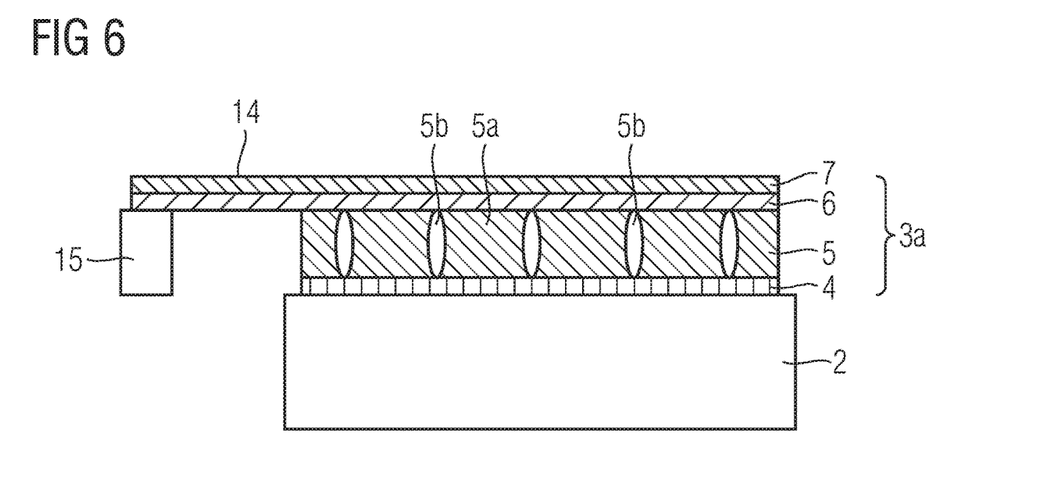
FIG. 6 in diagram form, is a concept for a further electrode according to an embodiment of the invention.

FIG. 6 shows, by way of example, an embodiment of a further electrode 3a according to the invention on a converter material 2 with a voltage source 15. The counting X-ray detector 1 comprises in a stacked array a converter material 2 for converting X-ray radiation into electric charges, and a further electrode 3a. On the side of the converter material 2 facing the beam, the further electrode 3a is provided as a cathode. The further electrode 3a is planar in design. The further electrode 3a and the converter material 2 are electrically connected to one another in a planar manner. The further electrode 3a and the converter material 2 can at least approximately have the same planar expanse. The further electrode 3a is designed to be at least partly transparent. The further electrode 3a can be at least partly transparent or have low absorption, for example to X-ray radiation, UV, IR, or visible light. Preferably, the further electrode 3a can be at least partly transparent or have low absorption to X-ray radiation and IR light. The further electrode 3a is at least partly transparent to IR, UV, or visible light and the properties of the converter material 2 can be optimized via additional irradiation of IR, UV, or visible light. The further electrode 3a can be designed to be at least partly transparent to UV, IR, or visible light such that a maximum of 30 percent of the irradiated UV, IR, or visible light is absorbed. The further electrode 3a can be at least partly electrically conductive. The further electrode 3a comprises a plurality of layers in a stacked array. The layers are connected to each other in a planar manner. The further electrode 3a comprises the following layers in the following sequence: an electrically conductive contact layer 4, an electrically conductive first intermediate layer 5, an electrically conductive high voltage layer 6 that is designed in the form of a mesh and a first carrier protection layer 7. The contact layer 4 can be electrically connected directly to the converter material 2. The electrically conductive contact layer 4 is applied directly onto the converter material 2. The electrically conductive first intermediate layer 5 is applied directly onto the electrically conductive contact layer 4. The electrically conductive high voltage layer 6 is applied directly onto the electrically conductive first intermediate layer 5. The first carrier protection layer 7 is applied directly onto the electrically conductive high voltage layer 6. The electrically conductive high voltage layer 6 of the further electrode 3a is designed in the form of a mesh. The electrically conductive high voltage layer 6 is an electrically conductive mesh 16.

Figure 7:
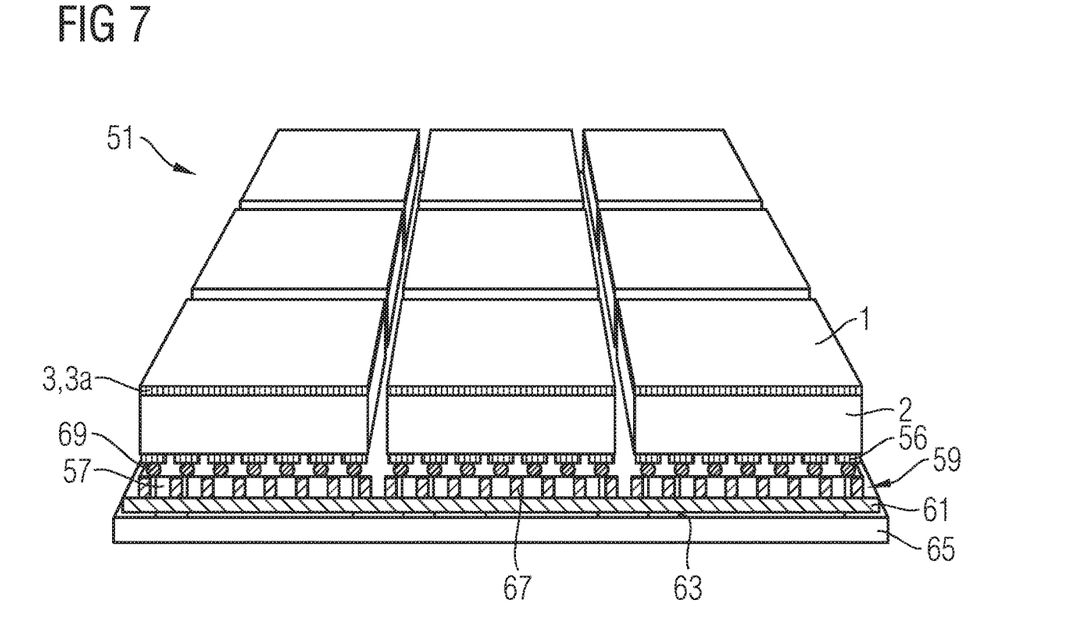
FIG. 7 in diagram form, is a detector module comprising an arrangement of X-ray detectors according to an embodiment of the invention.

FIG. 7 shows, by way of example, an embodiment of the detector module 51 with an array of X-ray detectors 1 according to the invention. In a preferred embodiment, the X-ray detector 1 comprises a two-dimensional matrix or array consisting of a plurality of pixels or sub-pixels. The number of sub-pixels can be for example in the region ranging from 100 to several thousands. The X-ray detector 1 comprises a converter material 2. The converter material 2 can be designed as a planar direct converter, comprising for example CdTe, CZT, CdZnTeSe, CdTeSe, CdMnTe, InP, TlBr$_2$, HgI$_2$, GaAs or other materials. The upper side of the converter material 2 comprises an electrode 3 or a further electrode 3a. The underside of the converter material 2 comprises a two-dimensional array of contacts 56. The contacts 56 are connected via soldered connections 69 to the readout contacts 57 and to the pixel electronics 67 in the readout and/or evaluation unit 59. The soldered connections 69 can be designed, for example, as bump bonds or soldered material in conjunction with copper pillars. The number of contacts 56, the number of soldered connections 69, the number of readout contacts 57, and the number of pixel electronics 67 in the readout and/or evaluation unit 59 is the same. The electric field between the electrode 3 or the further electrode 3a and a contact 56 determines a sensitive detection volume. The unit of a detection volume, a contact 56, a soldered connection 69, a readout contact 57 and a pixel electronics 67 connected to the readout contact 57 forms a pixel or sub-pixel. The readout and/or evaluation unit 59 is connected on the underside to a further substrate 61, for example a ceramic substructure or a carrier plate. The readout and/or evaluation unit 59 is connected via TSV-connections 63 running through the further substrate 61 to a peripheral electronics 65.

Figure 8:
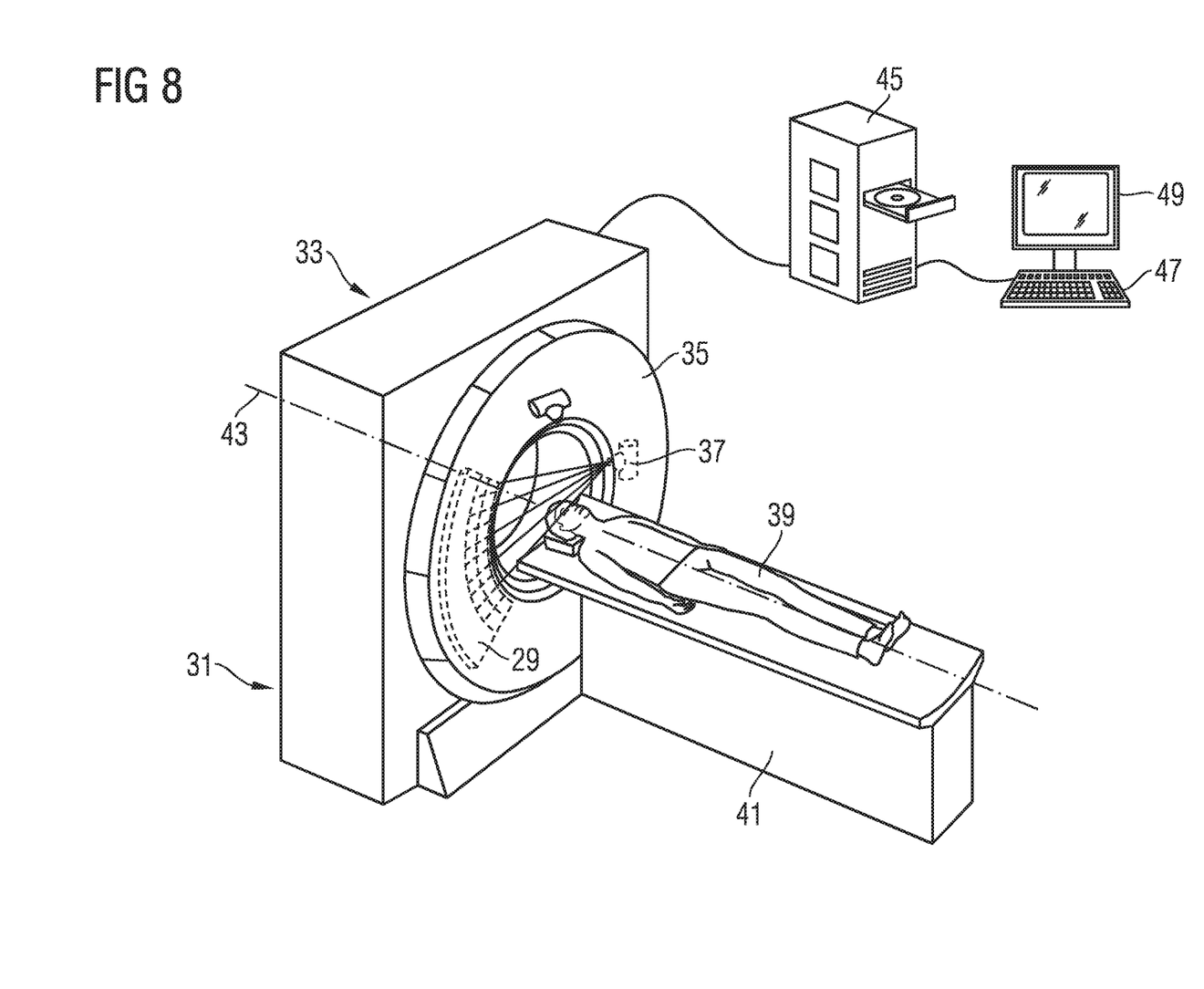
FIG. 8 in diagram form, is a representation of a computer tomograph according to an embodiment of the invention.

FIG. 8 shows, by way of example, an embodiment of the computed tomograph 31 according to the invention, with a detector device 29. The detector device 29 comprises the X-ray detector 1 according to the invention. The detector device 29 can comprise a plurality of detector modules 51 which have at least one X-ray detector 1. The detector modules 51 preferably comprise a plurality of X-ray detectors 1 in a two-dimensional matrix or array. The computed tomograph 31 contains a gantry 33 with a rotor 35. The rotor 35 includes an X-ray source 37 and the detector device 29 according to the invention. The patient 39 is accommodated on the patient couch 41 and can be moved through the gantry 33 along the axis of rotation z 43. To control and calculate the sectional images, a computation unit 45 is used. An input device 47 and an output device 49 are connected to the computation unit 45.

Figure 9:
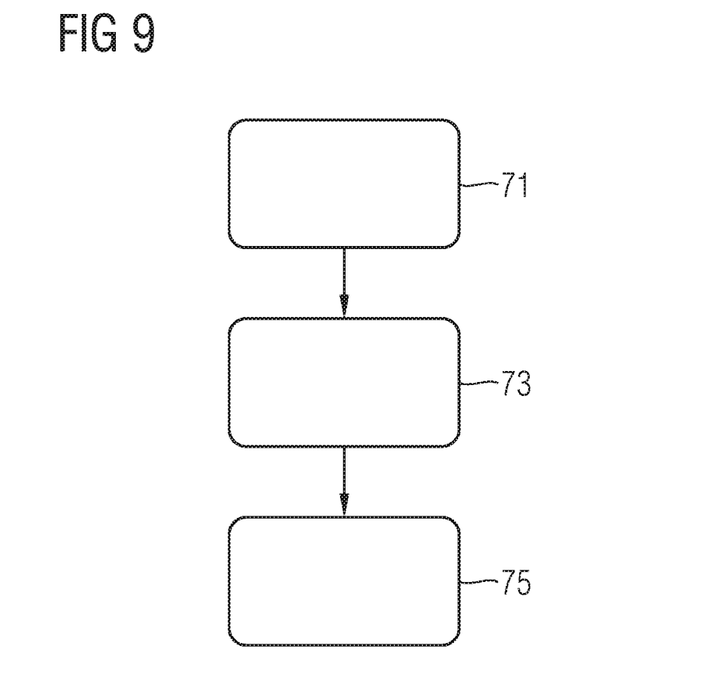
FIG. 9 in diagram form, is a representation of a method according to an embodiment of the invention.

FIG. 9 shows the method according to the invention for regulating the temperature of a converter material 2 of an X-ray detector 1 according to the invention. The method comprises the following steps: determination 71 of a first temperature, comparison 73 of the first temperature with a predetermined second temperature value, and adjusting 75 of a current passing through an electrically conductive heating layer 9 to regulate the temperature of the converter material 2. In the determination step 71, a first temperature is defined or measured via a temperature sensor 12, for example, on the side of the readout and/or the evaluation unit 59 or in the readout and/or the evaluation unit 59 that faces the converter material. In the comparison step 72, the first temperature is compared with the predetermined second temperature, by means, for example, of a comparator 13 in the readout and/or the evaluation unit 59. The comparison of the first temperature with the second temperature is carried out in a comparator 13 in the readout and/or the evaluation unit 59, for example an integrated circuit (Application Specific Integrated Circuit, ASIC). The second temperature can be a yardstick or a comparative value for a temperature in the converter material 2. In the adjustment step 75, the current passing through the electrically conductive heating layer 9 is adjusted to regulate the temperature or regulate the temperature of the converter material 2. In the event of a first temperature that is lower compared to the second temperature, the electric current or current flow through the heating layer 9 is increased. In the event of a first temperature that is higher compared to the second temperature, the electric current or current flow through the heating layer 9 is reduced. In the event of a first temperature that is the same compared to the second temperature, depending on the design of the comparator 13, the electric current or current flow through the heating layer 9 is increased or reduced or maintained at a constant value. The temperature in the converter material 2 is controlled, adjusted or regulated using the method according to the invention.

Although the invention has been illustrated in greater detail with the preferred embodiment, the invention is not restricted to the examples disclosed, and other variants can be derived therefrom by a person skilled in the art, without going beyond the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A counting X-ray detector comprising:
   a converter material to convert X-ray radiation into electric charges; and
   an electrode, the electrode being electrically conductively connected to the converter material and the electrode being designed to be at least partly transparent, the electrode including:
   an electrically conductive contact layer,
   an electrically conductive first intermediate layer,
   an electrically conductive high voltage layer,
   an second intermediate layer, and an electrically conductive heating layer, wherein the electrically conductive high voltage layer or the electrically conductive heating layer is designed as an electrically conductive mesh.

2. The X-ray detector of claim 1, wherein the electrode further includes a first carrier protection layer arranged in a region of the high voltage layer or a second carrier protection layer arranged in the region of the heating layer.

3. The X-ray detector of claim 1, wherein an electric circuit is provided to apply a current to the electrically conductive heating layer as a function of a first temperature determined in the X-ray detector.

4. The X-ray detector of claim 3, further comprising:
a temperature sensor to acquire the first temperature on a side of the converter material that is opposite the electrode.

5. The X-ray detector of claim 4, further comprising:
a comparator to compare the first temperature with a second temperature value.

6. The X-ray detector of claim 1, wherein the electrically conductive high voltage layer or the electrically conductive heating layer is designed as a TCO layer.

7. The X-ray detector of claim 1, wherein the converter material comprises cadmium.

8. The X-ray detector of claim 1, wherein the electrically conductive mesh comprises at least one of copper, silver, nickel, and gold.

9. The X-ray detector of claim 8, further comprising:
an illumination device to illuminate the converter material.

10. The X-ray detector of claim 9, wherein the electrically conductive mesh is configured to absorb less than 30 per cent of an amount of light radiated by the illumination device onto the converter material.

11. The X-ray detector of claim 8, wherein the electrically conductive mesh absorbs less than 30 percent of an amount of light radiated by an illumination device onto the converter material.

12. The X-ray detector of claim 1, wherein the electrically conductive contact layer comprises one of: platinum, indium, molybdenum, tungsten, ruthenium, rhodium, gold, silver or aluminum.

13. The X-ray detector of claim 12, wherein the electrically conductive contact layer is designed to be at least partly transparent.

14. The X-ray detector of claim 1, wherein the electrically conductive contact layer is designed to be at least partly transparent.

15. The X-ray detector of claim 1, wherein the electrically conductive first intermediate layer comprises a bonding agent and an electrically conductive filler element.

16. The X-ray detector of claim 1, wherein the converter material and electrode are in a stacked array.

17. The X-ray detector of claim 1, further comprising:
a temperature sensor to acquire a first temperature on a side of the converter material that is opposite the electrode.

18. The X-ray detector of claim 17, further comprising:
a comparator to compare the first temperature with a second temperature value.

19. The X-ray detector of claim 1, further comprising:
an illumination device to illuminate the converter material.

20. The X-ray detector of claim 19, wherein the electrically conductive mesh is configured to absorb less than 30 per cent of an amount of light radiated by the illumination device onto the converter material.

21. A medical device comprising the counting X-ray detector of claim 1.

22. A method for regulating temperature of a converter material of a counting X-ray detector including the converter material and an electrode, the electrode being electrically conductively connected to the converter material and being designed to be at least partly transparent, the electrode including an electrically conductive contact layer, an electrically conductive first intermediate layer, an electrically conductive heating layer, and an electrically conductive high voltage layer designed in a form of an electrically conductive mesh, the method comprising:
determining a first temperature;
comparing the first temperature with a second temperature value; and
adjusting a current passing through the electrically conductive heating layer to regulate the temperature of the converter material.

23. The method of claim 22, wherein the electrode further includes:
an second intermediate layer
and wherein the method further comprises:
applying, via an electric circuit, a current to the electrically conductive heating layer as a function of a first temperature determined in the X-ray detector.

24. The method of claim 22, wherein the electrically conductive mesh comprises at least one of the following elements: copper, silver, nickel, gold.

25. The method of claim 24, wherein the electrically conductive mesh is configured to absorb less than 30 per cent of an amount of light radiated by an illumination device onto the converter material.

* * * * *